| United States Patent [19] | [11] Patent Number: 4,978,364 |
| --- | --- |
| Walker et al. | [45] Date of Patent: Dec. 18, 1990 |

[54] TRIIODIDE-PHOSPHORIC ACID STAIN AND METHOD FOR CELLULOSE FIBER EVALUATION

[75] Inventors: Hilary Walker, Marietta; Edward P. Bullwinkel, Roswell, both of Ga.

[73] Assignee: Kimberly-Clark Corporation, Neenah, Wis.

[21] Appl. No.: 455,464

[22] Filed: Dec. 22, 1989

[51] Int. Cl.$^5$ ............................................. C09B 67/00
[52] U.S. Cl. ........................................... 8/645; 8/633;
8/919; 162/162; 162/176; 252/408.1; 436/101; 436/103
[58] Field of Search .................... 8/645; 252/408.1

[56] References Cited

U.S. PATENT DOCUMENTS

| 3,984,341 | 10/1976 | Haschke et al. | 252/106 |
| --- | --- | --- | --- |
| 4,088,597 | 5/1978 | Morlock et al. | 252/106 |
| 4,444,756 | 4/1984 | Schlussler et al. | 252/106 |
| 4,487,752 | 12/1984 | Shimizu et al. | 423/507 |
| 4,676,931 | 6/1987 | Travis | 252/408.1 |

*Primary Examiner*—A. Lionel Clingman
*Attorney, Agent, or Firm*—Patrick C. Wilson

[57] ABSTRACT

A triiodide-phosphoric acid stain when applied to either moist or dry fiber samples produces a range of colors indicative of the fiber species and the degree of refining of the fiber. The stain is made from an aqueous triiodide solution of about 0.6M in potassium iodide and about 0.1M in iodine and is mixed with an acid solution about 77 percent by weight of phosphoric acid in a ratio of about 1 to 100 v/v of triiodide to acid just prior to its application to the fiber samples to be stained.

19 Claims, No Drawings

TRIIODIDE-PHOSPHORIC ACID STAIN AND METHOD FOR CELLULOSE FIBER EVALUATION

FIELD OF THE INVENTION

The present invention relates to stain solutions for fiber evaluation techniques. In particular, the present invention relates to a triiodide stain and method providing safe and quick stain preparation, extended shelf life and use in a one step method for staining of either wet or dry cellulose fiber samples.

BACKGROUND OF THE INVENTION

Various dyes have been used previously to develop contrasts between portions of a fibrous specimen studied with microscopic evaluation techniques. Information about the fiber sample may be determined by comparing the dyeing characteristics of the fibers to known characteristics. For instance, the presence and distribution of starch in the fiber may be determined by examining microscopically a dyed fibrous material. Prior to evaluation, the fibrous material is usually stained by immersion in a one percent aqueous or alcoholic solution of the dye. Such immersion is generally at room temperature or warmed for a period of time. The excess dye solution is washed and the fabric dried prior to evaluation.

An article entitled "Microscopical Techniques in Finishing Research" presented at the American Association of Textile Chemists and Colorists identified various solutions for staining fabrics prior to microscopic examination. For instance, iodine which colors starch purple or black may be used to detect the presence and uniformity of distribution of starch. The presence and location of polymeric impregnant can be shown because melamine resins can be dyed with several wool dyes, such as CI Acid Blue 1. Waxes may be colored with solvent dyes, and brief boiling of the fiber sample in 95 percent ethanol prior to staining enhances the depth of shade. Pectin and associated compounds yielding glucoronic residues on hydrolysis are stained by basic dyes. Proteins may be stained with acid or basic dyes depending on pH conditions.

Russian Pat. No. 127,462 describes examining paper fiber orientation by reflective light with a magnifying glass, microscope or other optical apparatus. The structure is shown more clearly if the sample is moistened with a three to five percent solution of hydrochloric acid and dried at 105° C. for five to ten minutes until the sample darkens.

Russian Pat. No. 444,072 describes a binder distribution determination method for nonwoven fabrics. A latex such as carboxylbutadiene-acrylonitrile SKN-40-1 GP is mixed with a 6.95 to 7.05 g/l dichlorotriazine reactive dye and then reacted at room temperature for about ten hours in the presence of sodium bicarbonate ($NaHCO_3$) before applying to the fabric. Such a compound may be used to impregnate black fabrics for analysis.

Russian Pat. No. 521,514 describes a method of determining the content of cotton seed shell in cotton fiber with ammonium molybdate which colors the tannin in the seed shell tissues. Where there is an intensive accumulation of tannin, which is a measure of the strength of the seed shell, the fiber sample assumes a dark orange color. Where the seed shell is less strong, i.e., the accumulation of tannin is small, the sample assumes a yellow color.

U.S. Pat. No. 3,190,724 describes testing cotton to determine damage by microorganisms. The test method moistens the fabric sample with a pH indicator solution substantially free of oxygen by using an inert propellent gas. The color of the indicator solution on the cotton sample is compared with the color of the indicator solution at various pH levels to determine the extent of damage, if any, to the cotton.

U.S. Pat. No. 3,576,713 describes a process of determining the ionic character of starches, wood pulps, paper masses, and paper surfaces by mixing them with solutions of organic coloring materials which show changes in the range of visible light in accordance with the ionic character of the materials. The reference describes using potassium salts of tetrabromo and tetraiododichlorofluorescein and coloring materials of triphenylmethane series, preferably chlorides of triamino and chlorides and oxalates of tetramethyltriphenylmethane.

Reliable microscopy requires that the cellulose fibers be stained. The Institute of Paper Chemistry discusses in Paper and Fiber Analysis various triiodide stains for microscopy work. Some triiodide stains use potassium triiodide and multicomponent salt solutions in a one-step application stain; another triiodide stain uses potassium triiodide and sulfuric acid in a two-step application. These multicomponent salt solution stains cannot tolerate even slight dilution with water and are limited to use on dried cellulose fiber samples. Such stains also are generally sensitive to light, have a relatively short shelf life and take some time to prepare. Further, preparation and use of the potassium triiodide sulfuric acid stain is potentially hazardous.

Known triiodide stains generally involve the use of concentrated aqueous salt solutions. For example, some of the more widely used triidido stains are Graff "C" stain, the Herzberg stain, the Sutermeister, the Jenke stain, and the Selleger stain. The Graff "C" stain is made by the addition of potassium triiodide solution to a concentrated mixture of aluminum chloride, calcium chloride and zinc chloride solutions. The Herzberg stain combines potassium triiodide solution with a concentrated zinc chloride solution. The Sutermeister stain is made by adding potassium triiodide solution to a saturated calcium chloride solution. The Jenke stain combines solutions of potassium triiodide and saturated magnesium chloride. The Selleger stain is a mixture of potassium triiodide solution and a concentrated calcium nitrate solution. As mentioned above, these stains are impractical to use on wet fibers because any dilution of the stain with water renders the stain inoperative. These stains have other drawbacks which limit their usefulness. One problem is that the triiodide stains are unstable. For example, the stains are light sensitive and easily oxidized. The stains must therefore be stored in a refrigerator in small quantities in stoppered dark glass bottles to minimize the air oxidation and the light degradation of the stain.

Thus, there exists a need in the art for a stain solution for fiber evaluation that is free of the problems typically found when preparing and using fiber evaluation stains.

SUMMARY OF THE PRESENT INVENTION

The present invention solves the above-described problems by providing an easily prepared and used triiodide phosphoric acid stain. Generally, the present invention provides a stain for cellulose fiber made from a triiodide solution of potassium iodide and iodine mixed with phosphoric acid just prior to use. More specifically described, the stain uses a triiodide solution with a molar ratio of iodide to iodine in the range of 1 to 10 in an acid solution of about 72% to about 82% by weight of phosphoric acid to provide a triiodide stain with a molar content in the range of 0.0006 to about 0.0017 molar triiodide.

The stain of the present invention when stored as a two component system of triiodide solution and acid solution has a shelf life limited only by the life of the components. The stain resulting from mixing the two component solutions may be reliably applied to either wet or dry cellulose fiber samples.

Accordingly, it is an object of the present invention to provide a triiodide-phosphoric acid stain for fiber evaluation.

It is another object of the present invention to provide a triiodide-phosphoric acid stain that is relatively safe to prepare.

It is an object of the present invention to provide a triiodide-phosphoric acid stain that is easily and quickly prepared prior to use.

It is a further object of the present invention to provide a triiodide-phosphoric acid stain for use in a one step method for staining.

It is an object of the present invention to provide a triiodide-phosphoric acid stain for use with either wet or dry cellulose fiber samples.

It is yet another object of the present invention to provide a triiodide-phosphoric acid stain which tolerates slight dilution with water.

It is still a further object of the present invention to provide a triiodide-phosphoric acid stain which is not light sensitive.

It is another object of the present invention to provide a triiodide-phosphoric acid stain which is not easily oxidized.

It is an object of the present invention to provide a triiodide-phosphoric acid stain in which changes in the concentration of phosphoric acid causes changes in the color which cellulose fibers stain.

It is another object of the present invention to provide a triiodide-phosphoric acid stain in which changes in the concentration of the triiodide solution changes the intensity of the color which the fiber stains.

It is an object of the present invention to provide a triiodide-phosphoric acid stain which differentiates degrees of refining of cellulose fibers.

It is an object of the present invention to provide a triiodide-phosphoric acid stain which may be used to examine and determine fiber content of papers made with different types of cellulose fibers.

It is an object of the present invention to provide a triiodide-phosphoric acid stain which may be used to analyze the soft wood fraction in paper sheet.

Still other objects, features and advantages will become apparent upon reading the following detailed description of the present invention, the examples and the appended claims.

DESCRIPTION OF THE PREFERRED EMBODIMENTS

The present invention provides an easily prepared and used triiodide-phosphoric acid stain. The stain of the present invention when stored as a two component system of solutions has a shelf life limited only by the life of the components. The stain resulting from mixing the two component solutions may be reliably applied to wet or dry cellulose fiber samples.

The stain of the present invention is prepared by mixing two solutions. The first solution is a triiodide solution of about 0.6M in potassium iodide and about 0.1M in iodine. The second solution is about 77 percent by weight phosphoric acid. The two solutions are preferably stored separately. The two solutions are mixed together in a ratio of about 1 to 100 v/v of triiodide to acid to yield the stain of the present invention. It is well known that acid-triiodide solutions are susceptible to air oxidation, but that neutral triiodide solutions are stable in the presence of air. The stain can be used in all cases where conventional triiodide stains are used and in particular overcomes deficiencies of prior triiodide solutions because the stain may be applied to either moist or dry fiber samples. The stain produces a range of colors on the fiber sample indicative of the degree of refining of the fiber.

The working range for the phosphoric acid concentration is between about 72 to about 82 percent by weight; the preferred concentration is about 77 percent. Changes in the concentration of phosphoric acid cause changes in the color which the cellulose fibers are stained. Changes in the concentrations of the triiodide solution changes the intensity of the color which the fibers are stained.

The triiodide-phosphoric acid stain of the present invention is prepared quickly and the present invention provides an easy to use stain for evaluation of cellulose fibers. The stain components have an extended shelf life, and when combined may be used to stain either wet or dry cellulose fiber samples.

A preferred embodiment of the present invention uses potassium iodide to prepare the triiodide solution. This salt has a water solubility which permits the iodide anion to be in solution in sufficient quantity to combine with the iodine and form triiodide. Other soluble salts of iodide, such as, alkali metal salts or alkaline earth salts, which provide the iodide anion in solution can be used for a stain within the teachings of the present invention.

EXAMPLE 1

Variation of Stain Intensity With Variation of Triiodide Concentration

Varying the triiodide concentration varies the intensity of coloring on the cellulose fibers. The test stains were prepared from a 0.6M potassium iodide solution mixed with a 0.1M iodine solution. The concentration of the potassium iodide was purposely kept in excess of the iodine concentration to insure the formation of the triiodide anion. To push the reaction toward formation of the triiodide anion, the ratio of iodide to iodine preferably is greater than one and could range up to 1 to 10. The concentration of the phosphoric acid was nominally around 75%.

Three stains were prepared: 0.002M potassium triiodide in 70% by weight phosphoric acid; 0.001M potassium triiodide in 77% by weight phosphoric acid; and 0.0001M potassium triiodide in 74% by weight phosphoric acid. Slides of flax fibers were prepared by drawing on a glass slide a small aliquot of a suspension of flax fibers in water. The slides were dried by heating on a warm hot plate. Each of the triiodide stains were added to the flax fibers on a glass slide and the color intensity of the stain fibers were recorded. The results are presented in Table 1.

As shown in Table 1, a weak concentration of triiodide stain solution applied to fibers results in a fiber stain color which was too pale to distinguish the morphology of the fiber. A too concentrated triiodide stain solution applied to the flax fibers resulted in the fibers being stained so darkly that the fiber morphology was no longer recognizable and thus prevented fiber identification.

Additional potassium triiodide stains were studied using the above described technique. The additional stains were used to define the limits of staining intensity sufficient to permit identification of fiber morphology. It was determined that at about 0.0006M potassium triiodide, the stain was sufficiently intense to identify fiber markings, while concentrations in excess of about 0.0017M potassium iodide provided fiber colors too intense for clearly distinguishing the fiber morphology.

TABLE 1

Stain Color Intensity vs. Triiodide Concentration

| $I_3$ Concentration | $H_3PO_4$ Concentration | Intensity of Stain of Flax |
|---|---|---|
| .0001 M | 74% | Colors too pale to identify fiber morphology |
| .0006 M | 77% | Color intensity strong enough to identify fiber markings |
| .001 M | 77% | |
| .0017 M | 76% | |
| .002 M | 70% | Colors too dark to identify fiber morphology |

EXAMPLE 2

Dependence of Stain Coloration On Phosphoric Acid Concentration

Another experiment was conducted to determine the effect of varying the phosphoric acid concentration. The triiodide stain again was prepared with a 0.6M concentration of potassium iodide and 0.1M iodine solution. The volume of phosphoric acid in the stain was varied to change the concentration, and the triiodide concentration was held constant.

Four stains were prepared with each stain having a triiodide concentration of 0.001M. The phosphoric acid concentrations were 53%, 71% and 85%. Each stain was tested on a range of cellulose fiber species dried on glass slides.

It was observed that at 85% phosphoric acid certain types of cellulose fibers began to dissolve. There was no color difference between the flax bast and shive as both stained blue. At about 77% concentration, the phosphoric acid gave good color differentiation; e.g., cotton linters and flax bast stained red, abaca stained grey-red, and flax shive and bleached softwood fibers stained blue.

At about 71% concentration, stain color differences on the fibers could still be discerned, but the intensity of the color was less strong. Now the blue color in the flax shive exhibited a grey tint. With about 53% phosphoric acid, the intensity of colors were much fainter. Abaca, softwood and flax stained tan while the flax bast stained faint red. The following Table 2 reports the color response for different fiber samples at the different acid concentrations.

TABLE 2

Stain Color versus Phosphoric Acid Concentration

| | Concentration % By Weight $H_3PO_4$ | | | |
|---|---|---|---|---|
| Fiber Sample | 53% | 71% | 77% | 85% |
| Abaca | tan | | purple | |
| Softwood | tan | | blue | |
| Cotton | | | red | |
| Highly Refined Cotton | | | blue | |
| Flax shive | tan | blue-gray | blue | blue-dissolves fiber |
| Flax Bast | faint red | faint red | red | blue-dissolves fiber |

EXAMPLE 3

Fiber Refining Analysis

The stain of the present invention may be used also to differentiate degrees of refining of cellulose fibers. It was noted at about 77% phosphoric acid, certain fibers, such as bleached cotton linters and larger diameter flax bast fibers, stained red. Smaller diameter bast fibers stained from tan to blue/grey in color depending on the fiber diameter size.

This phenomenon of change in stain color with change of fiber diameter size was used to study the changes in stain coloration of bleached cotton linters with the degree of refining to which the cotton linters were subjected. Bleached cotton linters were refined in a PFI Mill Model SKF 1207J manufactured by the Norwegian Pulp and Paper Institute of Oslo, Norway. The refining was carried out using a beating pressure of approximately 3.4 kg/cm and was stopped after a completion of 2,000 revolutions, 10,000 revolutions, and 35,000 revolutions so that small samples of the refined cotton linters could be removed from the mill. These samples were stained using the 0.001M triiodide in 77% phosphoric acid stain and examined at 100 power magnification with a light microscope.

Table 3 reports the stain color for cotton linters subjected to different degrees of refining. The results indicate that the triiodide stain of the present invention may be used in conjunction with visual assessment of cotton fiber appearance to indicate the degree of refining to which the fiber has been subjected.

TABLE 3

0.001 M Triiodide Stain in 77% $H_3PO_4$ vs. Degree of Refining

| Degree of Refining | Fiber Stain Color |
|---|---|
| None | Red |
| 2,000 PFI Revolutions | Ref fiber with few blue fibrils |
| 10,000 PFI Revolutions | Red fiber with many blue fibrils |
| 35,000 PFI Revolutions | Tan red fiber with very high amounts of blue fibrils |

EXAMPLE 4

Examination of Fiber Content of Papers Made With Different Types of Cellulose Fibers Approximately 0.1 gram samples of paper were taken and the actual weights recorded. Using standard procedures such as that described in the Paper Institute Handbook, the coating or sizing on the paper was removed. The paper samples were rinsed in water before pulping with a Waring® blender which has the blades purposely dulled so that the fibers were separated but not cut.

The fiber dispersions were brought up to 1000 ml by adding water. While the fibers were in suspension, two 10 ml aliquots were poured into centrifuge tubes. The fibers were centrifuged down and the clear supernatant water carefully removed.

A portion of the stain of the present invention was added to the damp fibers in the centrifuge tubes to stain them. In this instance, 2.49 g potassium triiodide was dissolved in 20 ml of water and 0.635 g iodine was added. The volumetric flask was shaken to dissolve the iodine and to form the triiodide ion. The volume was then brought up to 25 ml with additional water. A 77% phosphoric acid solution was prepared by mixing 850 ml of concentrated 85% phosphoric acid with 150 ml of water. Prior to staining the damp cellulose fibers in the centrifuge tubes, 0.4 ml of the 0.1M potassium triiodide solution were added to the 40 ml of 77% phosphoric acid.

The stained fibers were transferred using the rest of the 40 ml triiodide solution to a Millipore ® filtering apparatus with a metal grid support in the funnel. The filtering apparatus included a Millipore ® filter pad such as RAWG 04700 1.2 μm. A vacuum was applied and the fibers were pulled down in a random pattern onto the Millipore ® filter pad. The filter pad was removed, placed onto a transparent Millipore ® holder and mounted on a microscope stage. The filter pad was examined at 100X magnification. Table 4 lists the fibers tested and their stain color.

TABLE 4

Color Stain of Fibers Following Application of Dilute Triiodide Stain

| Fiber | Color |
| --- | --- |
| Softwood | Blue |
| Hardwood | Grey |
| Esparto | Red/Grey |
| Abaca | Red/Grey |
| Sisal | Red/Grey |
| Cotton | Red |
| Flax Bast | Red/Brown |
| Flax Shive | Blue |

The percentage of specific types of fibers in a paper sample may be determined. To do this, the stained fibers on the Millipore ® filter pad are counted by determining the number of times a specific type of fiber crosses the lines of the grid included in the microscope eyepiece.

A procedure for counting fibers is described in *The Fiber Crossing Method* by Brady, Berrins and Clark, TAPPI, 39, No. 1, 40 (1956). One milligram of sample on a 47 mm diameter filter pad gives an easily countable amount. The fiber crossings are determined for each type of fiber in the field of vision. The stain of the present invention helps differentiate the fiber types. The microscope holder for the filter is then moved to a new field of vision, and the fiber crossings for each type of fiber again are counted. The fiber crossing counts are determined for a total of twenty instances. The number of crossings for each fiber type for the twenty counts are averaged, and the amount of specific fibers is calculated from a previously determined fiber factor for each type of fiber. The fiber factor (expressed as crossings/grid/mg) is obtained by essentially following the same procedures described above, but using a known pulp of 100% of the specific species to be analyzed.

EXAMPLE 5

Analysis of Wood Pulp In Paper Sheet

The stain of the present invention is useful for analyzing the softwood (sw) fraction in a paper sheet comprising a blend of known hardwood and softwood fibers. Such papers include cigarette papers, teabags, writing papers, and the like. The fractional components of such papers are tested for a number of reasons, including determination of the quality of the paper and monitoring of the manufacturing processes. Such analysis may be conducted for cellulose fiber paper samples if the fiber factors are known for the specific species under consideration.

To determine the fiber factor, a sample paper made of the specific species is first pulped using the Waring ® blender method as described in Example 4. For this example, assume a 100.4 mg sample of the paper made from the species to be analyzed is pulped to form a pulp slurry. The final volume of the pulp slurry is brought to 1000 ml by adding water. Following vigorous shaking and with the fibers in suspension, an aliquot of the slurry is withdrawn into a centrifuge tube and centrifuged. More than one aliquot would be withdrawn and evaluated following these steps, depending upon the confidence level necessary for the analysis of the softwood fraction in the hardwood/softwood paper blend. In the present example, assume one aliquot of 9.2 ml is withdrawn into a centrifuge tube and centrifuged. The supernatant water is decanted.

The damp fibers at the bottom of the centrifuge tube are stained with a small portion of the triiodide-phosphoric acid stain of the present invention. Then the fibers are tranferred from the centrifuge tube to a filter system and pad, such as a Millipore ® filtering system set up with an RAWG 04700 1.2 μm filter pad. The stain of the present invention is used as a wash to help transfer the fibers to the filter pad. A vacuum is applied and the fibers are pulled down in a random pattern on the Millipore ® filter pad. The filter pad is then placed in a clear Millipore ® plastic pad holder and placed on the microscope stage.

The average softwood crossing factor per milligram of softwood pulp is determined for each aliquot sample, as described in Example 4. Under 100 power magnification, the average softwood crossing counts for a number of sampling areas is obtained for each aliquot sample. Continuing the present example, assume 20 sampling areas average 49.9 crossings for the 9.2 ml aliquot.

The weight of the pulp on the filter pad is then determined. The 100.4 mg softwood pulp in 1000 ml of water equals 0.1004 mg pulp per ml of suspension. Therefore, the 9.2 ml aliquot would result in a filter pad containing about 0.92 mg softwood fibers. The average crossing count for the aliquot is then divided by the weight of the pulp held on its pad to determine the softwood factor for the paper sheet, i.e., the number of fiber crossings per milligram of paper.

49.9 grid crossings ÷ .92 mg = 54 grid crossings per milligram softwood pulp for the 9.2 ml aliquot sample.

The softwood factor for each aliquot is summed together and an average is determined. Assume a second aliquot was drawn, counted and found to have 55.5 grid crossings per milligram softwood pulp. The average softwood factor in the present example is determined to be about 55 grid crossings per milligram softwood pulp.

Before analyzing the paper sheet for fractional softwood content, the moisture content of the sheet is determined. First, a sample of the paper sheet is dried at 110° C. until a constant weight is obtained. For example, assume that a 0.6158 g sample of the paper sheet is dried and results in a constant weight of 0.5659 g. The dry ratio is thus 0.5659 g ÷0.6158 g =0.919.

The paper sheet comprising the blend of known hardwood and softwood fibers is then analyzed to determine the softwood fraction. A sample of the paper sheet is weighed and pulped as described above in Example 4. The pulp slurry is dispersed in a known volume of water. Following vigorous shaking and with the pulp fibers in suspension, aliquots of the slurry are drawn into centrifuge tubes. Again, more than one aliquot may be drawn, depending on the requirements for the confidnece level for the testing. After centrifuging the aliquots, the supernatant water is decanted. The damp fibers are stained with the stain of the present invention. The hardwood and softwood fibers stain in differing colors to provide a visual difference between fiber types. The damp fibers are washed onto a filter pad, such as the Millipore ® pad discussed above and are randomly placed on the pad. The softwood fiber crossings are counted under microscope observation as described above in Example 4.

Continuing the present example, assume that a sample of the paper sheet weighing 101.0 mg is pulped and is dispersed in 500 ml of water. A samples of 10.0 ml is aliquoted into a centrifuge tube and centrifuged. The supernatant water is decanted, and the damp fibers in the tubes are stained with the triiodide-phosphoric acid stain of the present invention to contrast the hardwood and softwood fibers. The aliquot is filtered onto a Millipore ® pad, and the softwood fiber grid crossings are counted.

Using the determined dry ratio, the amount of fibers on a dry basis on the pad is determined to be 1.86 mg.

$$10.0 \text{ ml} \times 101 \text{ mg} \times 0.919 \div 500 \text{ ml} = 1.86 \text{ mg}$$

Using the fiber counting method described above, assume it is determined that the 10.0 ml aliquot has an average of 12.9 softwood crossings. The fractional amount of softwood in the paper sheet is then determined by dividing the average number of softwood crossings for the sample of the paper sheet by the computed softwood fiber factor for the known softwood in the sample.

12.9sw grid crossings ÷55sw grid crossings/mg=0.235 mg softwood in the 10.0 ml aliquout sample.

0.235 mg softwood sw÷1.86 mg dried paper sheet=12.6% by weight softwood fibers.

It is thus determined following these steps that the paper sheet contains about 12.6% softwood fibers by weight. This analysis is useful for manufacturing process control and quality control. The computed percentage of softwood content is compared with the expected content. Appropriate adjustments to the process may be made to bring the paper product into accordance with the tolerances for the fiber content of the paper sheet.

There has thus been provided, in accordance with the present invention, a fiber stain and method which accomplishes the objectives, aims and advantages set forth above. The principles, preferred embodiments and modes of operation of the present invention have been described in the foregoing specification. The invention is not to be construed as limited to the particular forms disclosed, because these are regarded as illustrative rather than restrictive. Moreover, variations and changes may be made by those skilled in the art without departing from the spirit of the invention as described by the following claims.

What is claimed is:

1. A stain solution to evaluate cellulose fibers, comprising:
    an aqueous triiodide solution of iodide and iodine, wherein the molar ratio of iodide to iodine is 1 or greater; and
    an acid solution from about 72 percent to about 82 percent by weight of phosphoric acid, wherein the triiodide solution and the acid solution are mixed together just prior to use to provide a triiodide stain with a molar content in the range of about 0.0006 to about 0.0017 molar triiodide.

2. The stain solution as recited in claim 1, wherein the ratio of iodide to iodine is in the range of 1 to 10.

3. The stain solution as recited in claim 1, wherein the triiodide solution is made from a metallic cation iodide salt and iodine.

4. The stain solution as recited in claim 3, wherein the metallic cation iodide salt is potassium iodide.

5. The stain solution as recited in claim 4, wherein the triiodide solution is about 0.6M in potassium iodide and about 0.1M in iodine.

6. The stain solution as recited in claim 5, wherein the acid solution is about 77 percent by weight of phosphoric acid.

7. A method of staining cellulose fiber prior to microscopic evaluation comprising applying to the cellulose fiber sample a stain of an aqueous triiodide solution of iodide and iodine wherein the molar ratio of iodide to iodine is 1 or greater mixed prior to use with an acid solution from about 72 percent to about 82 percent by weight of phosphoric acid to provide a triiodide stain with a molar content in the range of about 0.006 to about 0.0017 molar triiodide.

8. The method as recited in claim 7, wherein the ratio of iodide to iodine is in the range of 1 to 10.

9. The method as recited in claim 7, wherein the triiodide solution is made from a metallic cation iodide salt and iodine.

10. The method as recited in claim 9, wherein the metallic cation iodide salt is potassium iodide.

11. The method as recited in claim 10, wherein the triiodide solution is made from about 0.6M in potassium iodide and about 0.1M in iodine.

12. The method as recited in claim 11, wherein the acid solution is about 77 percent by weight phosphoric acid.

13. A method of staining cellulose fiber prior to microscopic evaluation comprising applying to the cellulose fiber sample a stain of triiodide solution of potassium iodide and iodine mixed with phosphoric acid in a ratio of about 1 to 100 v/v of triiodide to acid.

14. The method as recited in claim 13 wherein the concentration of the potassium iodide is greater than the concentration of the iodine.

15. The method as recited in claim 14 wherein the phosphoric acid solution is in a concentration of about 72 percent to about 82 percent.

16. The method as recited in claim 14 wherein the phosphoric acid solution is about 77 percent concentration.

17. The method as recited in claim 13 wherein the concentration of potassium iodide is about 0.6M and the concentration of iodine is about 0.1M.

18. The method as recited in claim 17 wherein the phosphoric acid solution is in a concentration from about 72 percent to about 82 percent.

19. The method as recited in claim 17 wherein the phosphoric acid solution is in a concentration of about 77 percent.

* * * * *

UNITED STATES PATENT AND TRADEMARK OFFICE
CERTIFICATE OF CORRECTION

PATENT NO. : 4,978,364
DATED : December 18, 1990
INVENTOR(S) : Hilary Wlaker and Edward P. Bullwinkel It is certified that error appears in the above-indentified patent and that said Letters Patent is hereby corrected as shown below:

Column 2, line 38, "triidido" should read --triiodide--;

Column 5, line 48, "71% and 85% should read --71%, 77%, and 85%--;

Column 9, line 20, "confidnece" should read --confidence--;

Column 5, line 25 "of Flax" should read --on Flax--;

Column 6, line 52, "Ref fiber" should read --Red fiber--;

Column 9, line 55, "aliquout" should read --aliquot--;

Column 10, line 65, "1 to 100" should read --1 to about 100--;

Signed and Sealed this

Eighth Day of June, 1993

Attest:

MICHAEL K. KIRK

Attesting Officer

Acting Commissioner of Patents and Trademarks